United States Patent
Borja et al.

(10) Patent No.: US 9,987,126 B2
(45) Date of Patent: Jun. 5, 2018

(54) CURVATURE-CHANGING, ACCOMMODATIVE INTRAOCULAR LENSES WITH EXPANDABLE PERIPHERAL RESERVOIRS

(71) Applicant: NOVARTIS AG, Basel (CH)

(72) Inventors: David Borja, Fort Worth, TX (US);
Lauren Gerardi, Des Plaines, IL (US);
Kevin M. Lewellen, Arlington, TX (US); Madison McEnery, Mansfield, TX (US); Benandria Williams, Fort Worth, TX (US)

(73) Assignee: Novartis AG, Basel (CH)

( * ) Notice: Subject to any disclaimer, the term of this patent is extended or adjusted under 35 U.S.C. 154(b) by 39 days.

(21) Appl. No.: 14/883,840

(22) Filed: Oct. 15, 2015

(65) Prior Publication Data
US 2016/0235523 A1 Aug. 18, 2016

Related U.S. Application Data

(60) Provisional application No. 62/116,758, filed on Feb. 16, 2015.

(51) Int. Cl.
*A61F 2/16* (2006.01)

(52) U.S. Cl.
CPC .......... *A61F 2/1635* (2013.01); *A61F 2/1648* (2013.01); *A61F 2250/0003* (2013.01); *A61F 2250/0018* (2013.01); *A61F 2250/0063* (2013.01)

(58) Field of Classification Search
CPC ............ A61F 2/1635; A61F 2002/1682; A61F 2002/169; A61F 2002/16901
See application file for complete search history.

(56) References Cited

U.S. PATENT DOCUMENTS

| | | | |
|---|---|---|---|
| 4,932,966 A | 6/1990 | Christie et al. | |
| 6,117,171 A | 9/2000 | Skottun | |
| 2003/0060878 A1* | 3/2003 | Shadduck | A61F 2/1613 623/6.13 |
| 2005/0119740 A1 | 6/2005 | Esch et al. | |
| 2006/0041307 A1 | 2/2006 | Esch et al. | |
| 2009/0005865 A1 | 1/2009 | Smiley et al. | |
| 2009/0319040 A1 | 12/2009 | Khoury | |
| 2010/0094412 A1 | 4/2010 | Wensrich | |
| 2011/0118834 A1 | 5/2011 | Lo et al. | |

FOREIGN PATENT DOCUMENTS

WO 2014/152017 A1 9/2014

\* cited by examiner

*Primary Examiner* — David Isabella

(57) ABSTRACT

An intraocular lens includes a deformable outer shell having a distal end and a proximal end, a fluid optic having at least one elastic membrane surface positioned to traverse an optical axis of a patient's eye and at least partially defining an internal chamber to hold an optical fluid, and an inner shell associated with the fluid optic having a distal end and a proximal end. Each end is joined to a corresponding end of the outer shell to define a reservoir between the inner and outer shells, the reservoir at least partially disposed about a circumference of the fluid optic and in fluid communication with the internal chamber. The deformable outer shell is configured to deform upon axial compression of the capsular bag in a manner that increases the volume of the reservoir and draws fluid from the chamber into the reservoir, modifying a curvature of the elastic membrane.

10 Claims, 2 Drawing Sheets

CURVATURE-CHANGING, ACCOMMODATIVE INTRAOCULAR LENSES WITH EXPANDABLE PERIPHERAL RESERVOIRS

FIELD

This present disclosure relates generally to the field of intraocular lenses (IOLs) and, more particularly, to accommodative IOLs.

BACKGROUND

The human eye in its simplest terms functions to provide vision by receiving light through a clear outer portion called the cornea, and focusing the image by way of a crystalline lens onto a retina. The quality of the focused image depends on many factors including the size and shape of the eye, and the transparency and focal power of the cornea and the lens.

When age or disease causes the lens to become less transparent, vision deteriorates because of the diminished amount of light that is transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by zonules. Relaxation of the ciliary muscle applies an axial force that tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus on both near and far objects.

As the lens ages, it becomes harder and is less able to change shape in response to movements of the ciliary muscle. This makes it harder for the lens to focus on near objects, a medical condition known as presbyopia. Presbyopia affects nearly all adults by the age of 45 or 50.

When a cataract or other disease requires the removal of the natural lens and replacement with an artificial IOL, the IOL typically is a monofocal lens that provides a suitable focal power for distance vision but requires the use of a pair of spectacles or contact lenses for near vision. Multifocal IOLs, e.g., relying on diffractive patterns to general multiple foci, have been proposed but to date have not been widely accepted.

Therefore, a need exists for a safe and stable accommodative intraocular lens that provides accommodation over a broad and useful range and an adjustable base power.

SUMMARY

The present disclosure relates generally to curvature-changing, accommodative intraocular lens (IOL). In certain embodiments, the IOL described herein is designed such that, upon implantation into the capsular bag of a patient's eye, axial compression of the capsular bag creates a negative pressure in an expandable peripheral reservoir of the IOL. This negative pressure may allow a fluid to be drawn into the expandable periphery from a fluid optic fluidly coupled thereto. This may cause a change in the curvature of an optical membrane of the IOL (i.e., a membrane traversing the optical axis), resulting in a change the refractive power of the IOL.

In certain embodiments, an intraocular lens configured to be implanted within a capsular bag of a patient's eye includes a deformable outer shell having a distal end and a proximal end, a fluid optic having at least one elastic membrane surface positioned so as to traverse an optical axis of the patient's eye and at least partially defining an internal chamber to hold an optical fluid, and an inner shell associated with the fluid optic having a distal end and a proximal end. Each end is joined to a corresponding end of the outer shell to define a reservoir between the inner and outer shells, the reservoir at least partially disposed about a circumference of the fluid optic and in fluid communication with the internal chamber. The deformable outer shell is configured to deform upon axial compression of the capsular bag in a manner that increases the volume of the reservoir and draws fluid from the chamber into the reservoir, modifying a curvature of the elastic membrane.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

Figure 1:
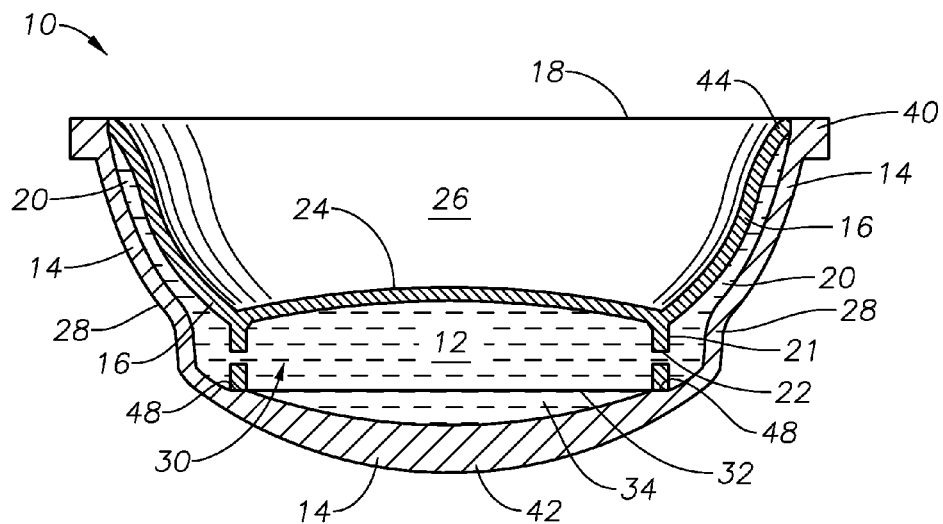
FIG. 1 is a cross-sectional, side view of an exemplary curvature-changing, accommodative intraocular lens, according to certain embodiments of the present disclosure.

FIG. 1 is a cross-sectional, side view of an exemplary curvature-changing, accommodative intraocular lens (IOL) 10, according to certain embodiments of the present disclosure. In certain embodiment, IOL 10 includes an outer shell element 14 and an inner shell element 16 nested within the outer shell 14. Outer shell 14 and inner shell 16 may define a variable volume reservoir 20, which may be in fluid communication with a chamber 12 of a fluid optic 30 via one or more outlets 22 in a sidewall 21. As a result, fluid contained in chamber 12 can pass to the reservoir 20 and vice versa. In the illustrated embodiment, the sidewall 21 is part of the inner shell 16 and the distal ends of the inner and outer shells are joined together by the lower rim 32 of the optic 30 that is seated upon an internal surface 48 of the distal end of the outer shell 14 in a fluid tight sealing engagement therewith. However, the present disclosure contemplates that sidewall 21 may alternatively be a separate element joined to the inner shell 16.

The proximal end 44 of the inner shell 16 may also joined to the corresponding proximal end 40 of the outer shell 14. In certain embodiments, a membrane 18 can span the proximal surface of IOL 10 to provide additional structural integrity or rigidity to the IOL 10. Additionally, membrane 18, inner shell 16, and elastic membrane 24 (discussed below) may form a fluid filled anterior chamber 26, which may affect the refractive power of the intraocular IOL 10. Further, the membrane 18 may also be an optic, e.g., a solid optic, to provide some of the overall refractive power of the intraocular IOL 10. Additionally or alternatively, refractive power can be provided by the shape and composition of the base 42 of the outer shell, which also spans the optical axis and, therefore, can also act upon light passing through the lens 10.

Figure 2:
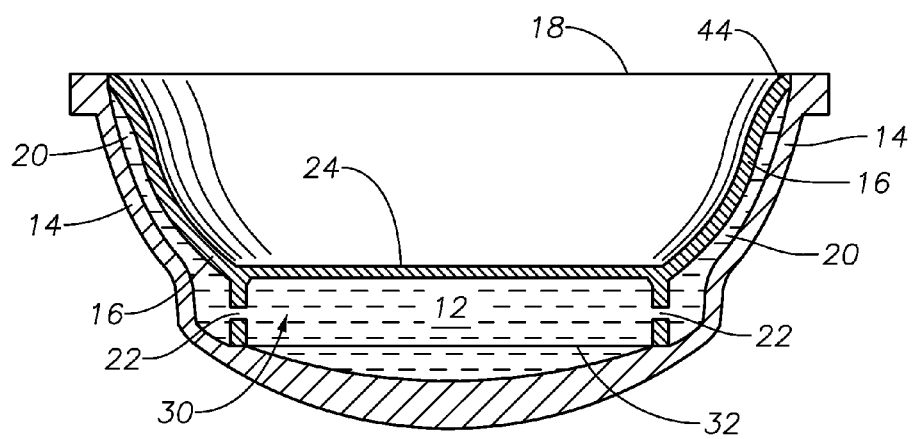
FIG. 2 is another cross-sectional, side view of the intraocular lens of FIG. 1, showing the lens in its disaccommodated (far vision) state.

In certain embodiments, IOL 10 may achieve accommodation via a curvature changing elastic membrane 24 of the fluid optic 30. As shown in FIG. 1, elastic membrane 24 may be formed so as to be naturally disposed in a convex shape. When implanted in the capsular bag of a patient's eye, axial compression of the capsular bag may deform the variable volume reservoir 20 in a manner that increases its volume. This volume increase may cause a negative pressure within variable volume reservoir 20, drawing fluid from chamber 12 into variable volume reservoir 20 via one or more outlets 22 in a sidewall 21. Comparing FIGS. 1 and 2, it can be seen that, as fluid in the chamber 12 flows to the reservoir 20, the elastic membrane 24 may go from its natural convex shape (as shown in FIG. 1) to a flatter shape (as shown in FIG. 2), thereby decreasing the refractive power of the fluid optic 30 and likewise decreasing the overall refractive power of IOL 10 (the illustrated changes in curvature depicted in FIGS. 1 and 2 are exaggerated for illustrative purposes).

In certain embodiments, outer shell 14 and inner shell 16 may each be constructed of the same material. As just one example, outer shell 14 and inner shell 16 may each be constructed from a resilient polymer, silicone, or acrylic, such as silicone or 2-phenyl ethyl acrylate and 2-pheylethyl methacrylate known under the name AcrySof®. In certain other embodiments, various components of IOL 10 may be constructed of different materials. As just one example, outer shell 14 and elastic membrane 24 of inner shell 16 may each be constructed from a resilient polymer, silicone, or acrylic, such as silicone or 2-phenyl ethyl acrylate and 2-pheylethyl methacrylate known under the name AcrySof®. In such embodiments, the remaining components of IOL 10 may be constructed of similar material but having a higher modulus of elasticity.

In certain embodiments, elastic membrane 24 may be constructed from a transparent amorphous polymer having a low glass transition temperature (Tg). For example, elastic membrane 24 may be constructed from a transparent amorphous polymer having a glass transition temperature below the standard body temperature of 37 degrees Celsius (which may allow for elastic membrane 24 to be a soft, elastic optical area).

Exemplary suitable fluids for use in the fluid optic 30 include fluids with an index of refraction higher than water, for example, an index of refraction greater than 1.3. In certain embodiments, the fluid may exhibit an index of refraction greater than 1.36 or greater than 1.38. In other embodiments, the index of refraction may be in the range of about 1.3 to about 1.8, in the range of about 1.36 to about 1.70, or in the range of about 1.38 to about 1.60. In embodiments including an anterior fluid filled chamber 26 (discussed above), the fluid contained therein may be an expandable (compressible) fluid having an index of refraction lower than that of fluid contained in reservoir 12 and variable volume reservoir 20.

Figure 3:
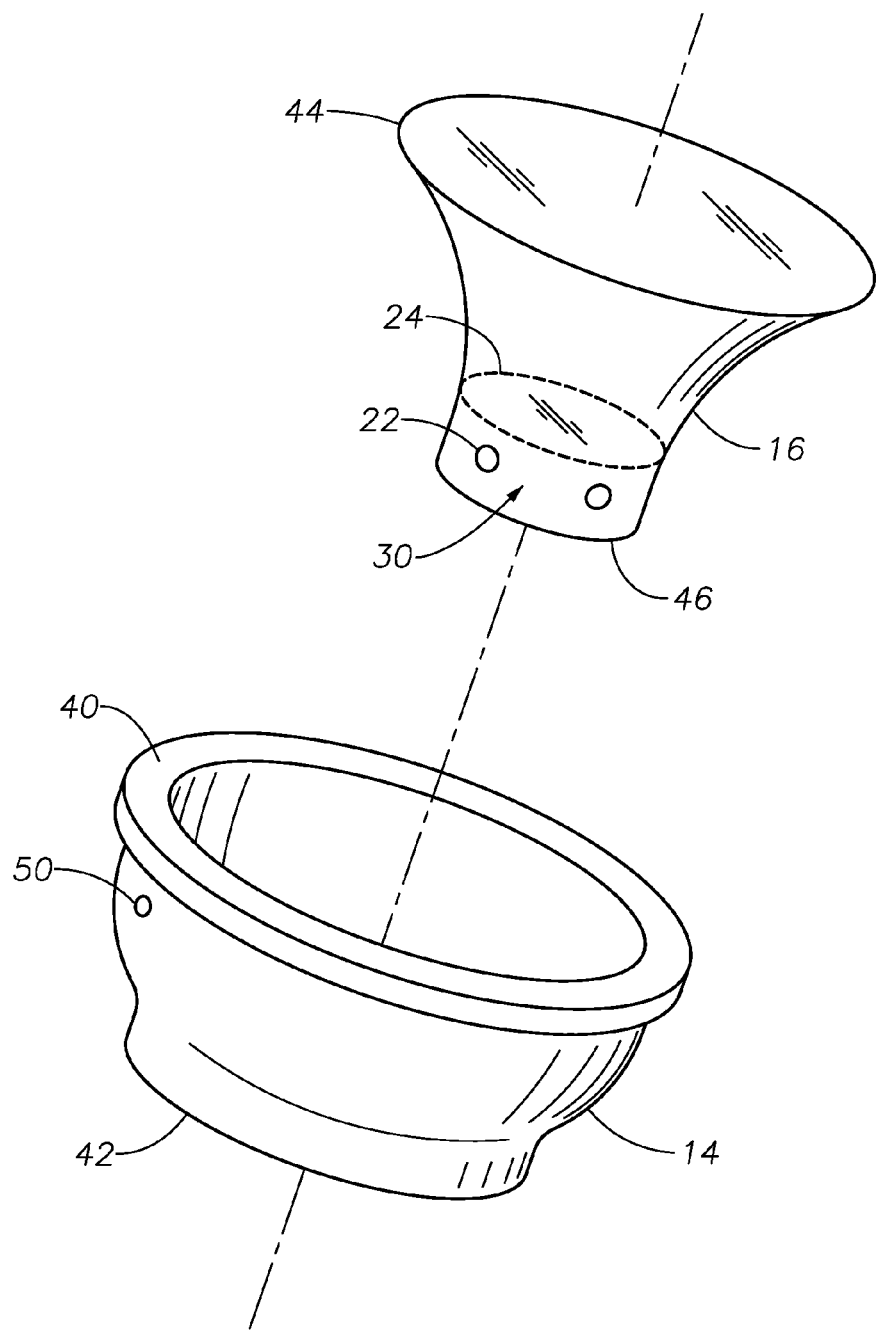
FIG. 3 is an exploded perspective view of the intraocular lens of FIG. 1.

FIG. 3 is an exploded perspective view of IOL 10 and illustrates the nesting relationship of inner shell 16 and outer shell 14. The inner shell 16 and fluid optic 30 can be integrally formed or they can manufactured separately and then joined together. In certain embodiments, it can be desirable to have a filling port 50 in the outer shell 14 such the inner and outer shells can be sealed together and then the variable volume reservoir 20 and chamber 12 can be filled with sufficient fluid to induce the desired initial (accommodated) shape to the membrane 24.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An intraocular lens configured to be implanted within a capsular bag of a patient's eye, comprising
a deformable outer shell having a distal end and a corresponding proximal end;
a fluid optic having at least one elastic membrane, that when implanted in the patient's eye is positioned so as to traverse an optical axis of the patient's eye, and the fluid optic at least partially defining an internal chamber to hold an optical fluid; and
an inner shell associated with the fluid optic having a distal end and a corresponding proximal end, each of the distal end and the corresponding proximal end of the inner shell joined to the corresponding distal end and proximal end of the outer shell to define a reservoir between the inner shell and the outer shell, the reservoir at least partially disposed about a circumference of the fluid optic and in fluid communication with the internal chamber of the optic;
wherein the deformable outer shell is configured to deform upon axial compression of the capsular bag in a manner that increases a volume of the reservoir and draws fluid from the chamber into the reservoir, modifying a curvature of the at least one elastic membrane, and
wherein the deformable outer shell is configured to deform upon release of the axial compression in a manner that decreases the volume of the reservoir and pushes fluid to the chamber from the reservoir.

2. The intraocular lens of claim 1, wherein the inner shell is flexible.

3. The intraocular lens of claim 1, further comprising a transparent element that spans the proximal end of the inner shell.

4. The intraocular lens of claim 1, wherein the inner shell and the at least one elastic membrane of the fluid optic are integrally formed.

5. The intraocular lens of claim 1, wherein the inner shell further comprises a cylindrical sidewall that provides an axial depth to the fluid optic.

6. The intraocular lens of claim 5, wherein the cylindrical sidewall of the inner shell further comprises at least one hole providing the fluid communication between the reservoir and the internal chamber of the optic.

7. The intraocular lens of claim 5 wherein the sidewall forms the distal end of the inner shell and is sealed to the outer shell.

8. The intraocular lens of claim 1, wherein the fluid optic comprises a separate element having at least a sidewall defining part of the reservoir and having at least one hole providing the fluid communication between the reservoir and the internal chamber of the optic.

9. The intraocular lens of claim 1, wherein the inner shell is joined to the fluid optic.

10. The intraocular lens of claim 1, wherein a sidewall of the fluid optic is sealed to the outer shell.

* * * * *